CHRYSANTHEMUM PLANT
Filed Aug. 13, 1971 2 Sheets-Sheet 1
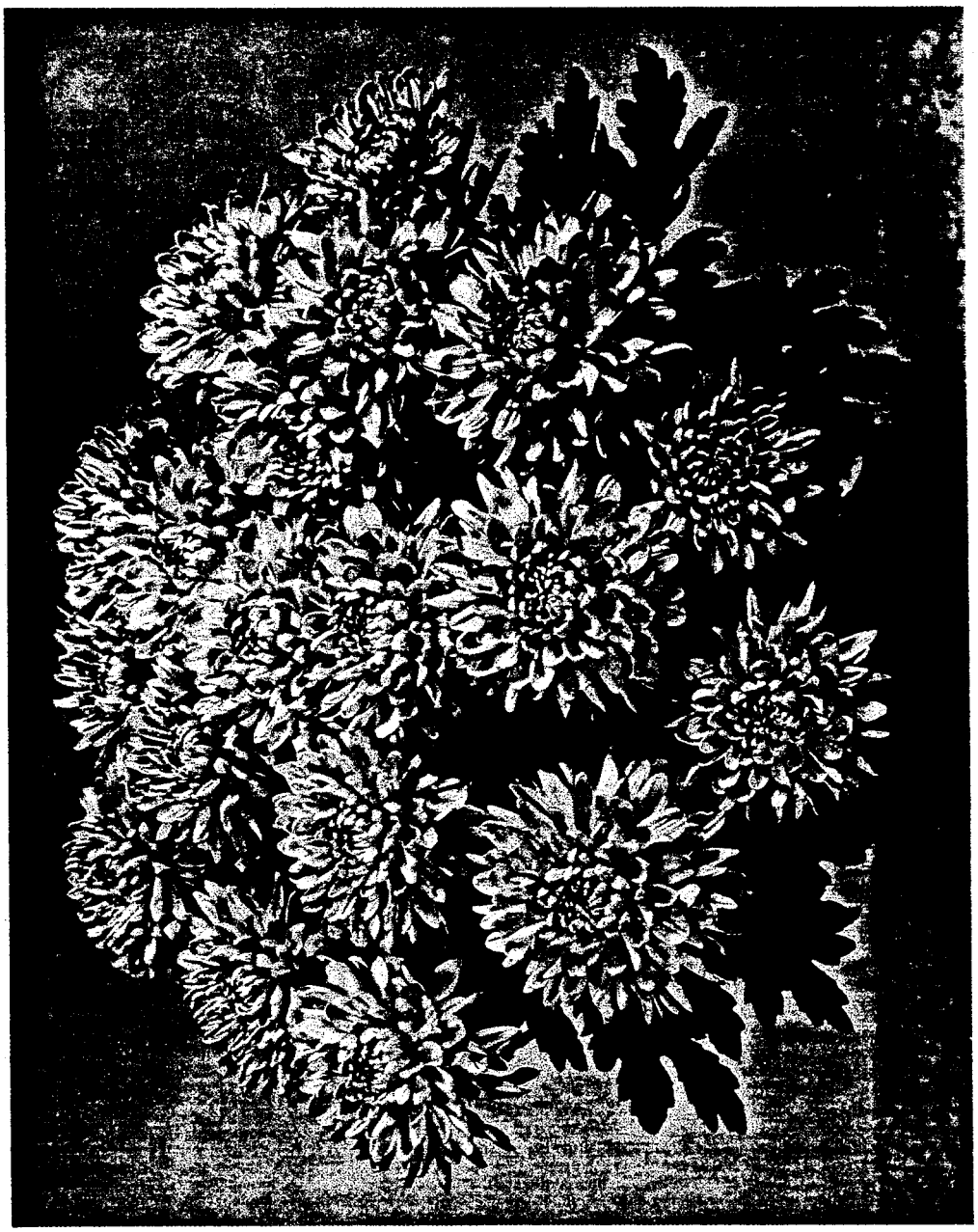

CHRYSANTHEMUM PLANT
Filed Aug. 13, 1971 2 Sheets-Sheet 2
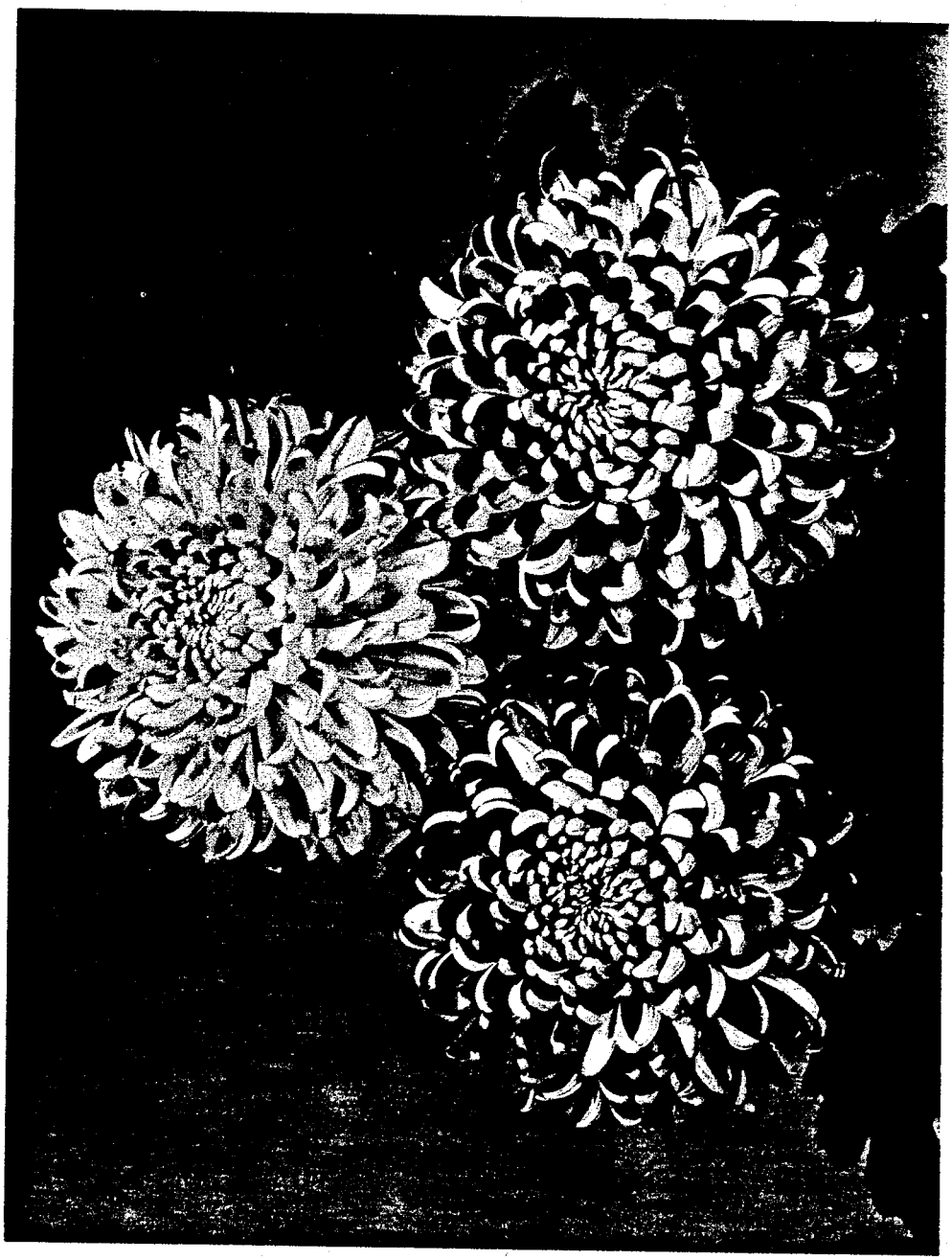

United States Patent Office

Plant Pat. 3,359
Patented June 12, 1973

3,359
CHRYSANTHEMUM PLANT

Walter H. Jessel, Jr., Doylestown, and William E. Duffett, Akron, Ohio, assignors to Yoder Brothers, Inc., Barberton Ohio

Filed Aug. 13, 1971, Ser. No. 171,782
Int. Cl. A01h *5/00*
U.S. Cl. Plt.—78 1 Claim

The present invention comprises a new and distinct cultivar of chyrsanthemum plant which is a sport of the cultivar known as Wildfire, disclosed and claimed in our copending application Ser. No. 93,922, filed Nov. 30, 1970, and now P.P. 3,236, assigned to Yoder Brothers, Inc., Barberton, Ohio, assignee of the present invention.

The new cultivar is similar in many respects to Wildfire, having the same characteristics of:

(1) Plant habit.
(2) Flower size and form.
(3) Foliage size, color and shape.
(4) Production either as a pot mum or standard.

The new cultivar is distinguished from Wildlife by its golden yellow color as compared to the generally bronze color of the parent, and a response 2–3 days earlier when grown under comparable conditions.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately a late 8 to early 9 week response when grown as a pinched pot mum or a single stem cut standard, and the following detailed description is based on observations made of the new cultivar in a greenhouse in Barberton, Ohio. The response time, blooming period, color, and total vigor may vary significantly with varying environmental conditions such as temperature, day length and light intensity.

Suggested flowering as a pot mum in the northern and western United States and coastal California is from May through October; in Florida, December through April, and in the southern United States, March through November.

Suggested flowering as a standard in the northern and western United States is from June through October; in coastal California, June through October; in Florida, December through April; and in the southern United States, May through November.

The accompanying photographic drawings show the unique characteristics of the new cultivar, with the color being as true as possible with color illustrations of this type. Sheet 1 illustrates the new cultivar as a pot mum, and sheet 2 comprises a comparison photograph of the new cultivar as a cut standard, with the new cultivar appearing at the top middle of the photograph, Wild Wind, disclosed and claimed in our pending application Ser. No. 153,456, on the left and the parent cultivar Wildfire on the right.

In the following description, color references are to the Munsell Color Book, 1963 edition, and comparisons are made with the parent cultiar Wildfire. Where only a single value or description appears for the new cultivar, such value or description applies also to the comparison cultivar Wildfire. It should be noted that difficulties were encountered in precisely determining the exact color keys, with those values listed comprising the closest available color keys.

Botanical classification: *Chrysanthemum morifolium*

| | Wild Honey | Wildfire |
|---|---|---|
| Bloom: | | |
| Size (as a cut standard) | 5¼″ | |
| Fully expanded (as a cut standard) | 5¾″ | |
| Borne | Singly on disbudded stems | |
| Stems | Strong | |
| Form | Semi-incurved | |
| Permanence | 10–14 days | |
| Color: | | |
| Center of flower | Golden yellow, 5Y8.5/10 | Light bronze, 5Y7/8 to golden bronze, 5Y7/10. |
| Base of petals | Golden yellow, 5Y8.5/14 | Red bronze, 5R3/8 to light bronze, 2.5Y6/8 over yellow, 5Y8.5/10. |
| Inside of petals | do | Do. |
| Reverse of petals | Golden yellow, 5Y8.5/10 | Light bronze 5Y7/8 to golden bronze, 5Y7/10. |
| Tonality from a distance | Golden yellow | Orange bronze. |
| Discoloration | do | Golden bronze. |
| Petals: | | |
| Texture | Smooth | |
| Appearance and form | Open at base, broad keel, tapering to a hooded point | |
| Arrangement | Composite, whorled on a single receptacle | |
| Persistence | Resist shatter | |
| Fragrance | Typical chrysanthemum | |
| Reproductive organs: | | |
| Stamen, anthers | None to 30 | |
| Pollen | None to scant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth: | | |
| (a) Pot mum | Semi-upright | |
| (b) Cut mum | Upright | |
| Height: | | |
| (a) Pot mum | Approximately 11″–13″ as a single pinched plant using 9 week Tall treatment timing as outlined in the Yoder Brothers, Inc. timetables for the various seasons of the year. | |
| (b) Cut mum | Approximately 36″ when grown on 13 week crop time with 4 long day weeks as outlined in the Yoder Brothers, Inc., timetables for the various seasons of the year. | |
| Spread: | | |
| (a) Pot mum | Approximately 8″ as a single pinched plant using 9 week Tall treatment timing as outlined in the Yoder mum timetables for the various seasons of the year. | |
| (b) Cut mum | None | |
| Foliage: | | |
| Top side | Dark green, 10GY3/4 | |
| Size: | | |
| (a) Pot mum | 5¼″ long, 2½″ wide | |
| (b) Cut mum | 7¼″ long, 3¾″ wide | |

Botanical classification: *Chrysanthemum morifolium*—Continued

| | Wild Honey | Wildfire |
|---|---|---|
| Foliage—Continued: | | |
| Quantity | Numerous | |
| Shape | Spatulate lobed | |
| Texture | Smooth | |
| Ribs and veins | Prominent | |
| Edge | Deeply indented | |
| Serration | Very slight | |
| Under side | Light green, 10GY5/4 | |
| Stipules | Prominent | |

We claim:

1. A new and distinct cultivar of chrysanthemum characterized particularly as to its uniqueness when compared to the parent cultivar Wildfire by its golden yellow flower color and by its 2–3 day earlier response when grown under comparable conditions.

No references cited.

ROBERT E. BAGWILL, Primary Examiner